(12) United States Patent
Basu et al.

(10) Patent No.: US 8,963,562 B2
(45) Date of Patent: Feb. 24, 2015

(54) TRANSDUCER CONFIGURATIONS AND METHODS FOR TRANSDUCER POSITIONING IN ELECTRICAL IMPEDANCE TOMOGRAPHY

(75) Inventors: Wrichik Basu, Bangalore (IN); Manoj Kumar Koyithitta Meethal, Bangalore (IN); Sakethraman Mahalingam, Bangalore (IN); Rajesh Veera Venkata Lakshmi Langoju, Bangalore (IN); Parama Ghoshal, Kolkata (IN)

(73) Assignee: General Electric Company, Schenectady, NY (US)

( * ) Notice: Subject to any disclaimer, the term of this patent is extended or adjusted under 35 U.S.C. 154(b) by 564 days.

(21) Appl. No.: 13/222,825

(22) Filed: Aug. 31, 2011

(65) Prior Publication Data

US 2013/0049770 A1   Feb. 28, 2013

(51) Int. Cl.
*G01R 27/28* (2006.01)
*G01N 27/02* (2006.01)
*G01N 33/28* (2006.01)

(52) U.S. Cl.
CPC .......... *G01N 27/026* (2013.01); *G01N 33/2823* (2013.01)
USPC ....................................................... 324/654

(58) Field of Classification Search
USPC ............... 73/861.08; 324/439–450, 600, 603, 324/605, 609, 629; 702/45, 47, 52, 53; 600/393, 547; 378/21
See application file for complete search history.

(56) References Cited

U.S. PATENT DOCUMENTS

| | | |
|---|---|---|
| 4,631,523 A | 12/1986 | Ono et al. |
| 4,751,842 A * | 6/1988 | Ekrann et al. ................ 73/61.44 |
| 5,309,912 A | 5/1994 | Knuttel |

(Continued)

FOREIGN PATENT DOCUMENTS

| | | |
|---|---|---|
| CN | 101344547 B  * | 3/2011 |
| WO | 9801069 A2 | 1/1998 |

OTHER PUBLICATIONS

D. Sankowski, et al., Mass Flow Measurements based on a Virtual Channel Concept, Proceedings of the 2005 5th International Conference on Intelligent Systems Design and Applications, 2005.*

(Continued)

*Primary Examiner* — Melissa Koval
*Assistant Examiner* — Daniel Miller
(74) *Attorney, Agent, or Firm* — Dean D. Small; The Small Patent Law Group (57) ABSTRACT

Transducer configurations and methods for transducer positioning in electrical impedance tomography are provided. A plurality of transducers for one electrical impedance tomography arrangement are configured for positioning proximate a surface of an object and spaced apart along the object, wherein the transducers are one or more conductive rings and have at least one non-conductive portion. The arrangement further includes one or more excitation drivers coupled to the plurality of transducers and configured to generate excitation signals for the plurality of transducers. The arrangement also includes one or more response detectors coupled to the plurality of transducers and configured to measure a response of the object at the plurality of transducers to the excitation applied by the plurality of transducers based on the excitation signals. The arrangement additionally includes a soft-field reconstruction module configured to reconstruct a property distribution based on the excitation signals and the measured response.

22 Claims, 7 Drawing Sheets

(56) References Cited

U.S. PATENT DOCUMENTS

| | | | |
|---|---|---|---|
| 5,367,911 A * | 11/1994 | Jewell et al. | 73/861.08 |
| 5,465,730 A | 11/1995 | Zadehkoochak et al. | |
| 5,820,558 A | 10/1998 | Chance | |
| 6,210,972 B1 * | 4/2001 | Williams et al. | 436/150 |
| 6,236,886 B1 | 5/2001 | Cherepenin et al. | |
| 6,310,478 B1 | 10/2001 | Heid | |
| 6,338,394 B1 | 1/2002 | Meynier | |
| 6,501,984 B1 | 12/2002 | Church et al. | |
| 6,940,286 B2 | 9/2005 | Wang et al. | |
| 7,429,248 B1 | 9/2008 | Winder et al. | |
| 2003/0216630 A1 | 11/2003 | Jersey-Willuhn et al. | |
| 2005/0109110 A1 | 5/2005 | Staszewski | |
| 2006/0253007 A1 | 11/2006 | Cheng et al. | |
| 2009/0084674 A1 * | 4/2009 | Holzhacker et al. | 204/286.1 |
| 2009/0093724 A1 | 4/2009 | Pernot et al. | |
| 2010/0097374 A1 * | 4/2010 | Fan et al. | 345/420 |
| 2011/0040176 A1 | 2/2011 | Razansky et al. | |
| 2011/0163770 A1 | 7/2011 | Mahalingam et al. | |
| 2012/0038368 A1 * | 2/2012 | Mahalingam et al. | 324/603 |
| 2012/0161782 A1 | 6/2012 | Ross | |
| 2013/0013239 A1 * | 1/2013 | Ross et al. | 702/66 |

OTHER PUBLICATIONS

Mohamad, et al., Electronic Design for Portable Electrical Capacitance Sensor: A Multiphase Flow Measurement, 4th International Conference on Mechatronics, May 2011.*

* cited by examiner

FIG. 20

TRANSDUCER CONFIGURATIONS AND METHODS FOR TRANSDUCER POSITIONING IN ELECTRICAL IMPEDANCE TOMOGRAPHY

BACKGROUND

The subject matter disclosed herein relates generally to data reconstruction systems and methods, and more particularly to transducer configurations for use in systems and methods to estimate properties of regions of interest, particularly in soft-field reconstructions of multi-material objects.

Soft-field tomography, such as Electrical Impedance Tomography (EIT), diffuse optical tomography, elastography, and related modalities may be used to measure the internal properties of an object, such as the electrical properties of materials comprising internal structures of the object. For example, in EIT systems, an estimate is made of the distribution of electrical conductivities of the internal structures. Such EIT systems reconstruct the conductivity and/or permittivity of the materials within the area or volume based on an applied excitation (e.g., current) and a measured response (e.g., voltage) acquired at or proximate the surface of the area or volume. Visual distributions of the estimates can then be formed.

In soft-field tomography, in particular EIT of a multi-material object, such as the flow of fluid including gas through a pipe, measurements are often performed on the horizontal flow through the pipe. In these horizontally oriented pipes, or any non-vertical pipes, the distribution of liquid and gas is not necessarily spread across the entire inner circumference of the pipe. For example, the level of flow through the pipe may vary, such that liquid flowing through the pipe settles towards the bottom of the pipe. Conventional transducer configurations and excitation methodologies, which are suited for symmetric geometries, such as flow in a vertical pipeline, are not optimally sensitive in this situation, namely where the pipe is not vertical.

BRIEF DESCRIPTION

In accordance with an embodiment, a soft-field tomography system is provided that includes a plurality of transducers configured for positioning proximate a surface of an object and spaced apart along the object, wherein the transducers are one or more conductive rings and have at least one non-conductive portion. The soft-field tomography system further includes one or more excitation drivers coupled to the plurality of transducers and configured to generate excitation signals for the plurality of transducers. The soft-field tomography system also includes one or more response detectors coupled to the plurality of transducers and configured to measure a response of the object at the plurality of transducers to the excitation applied by the plurality of transducers based on the excitation signals. The soft-field tomography system additionally includes a soft-field reconstruction module configured to reconstruct a property distribution based on the excitation signals and the measured response.

In accordance with another embodiment, a Soft-field tomography system is provided that includes a plurality of transducers configured for positioning proximate a surface of an object and spaced apart around an object, wherein at least a subset of the transducers are asymmetrically distributed relative to at least another subset of the transducers. The soft-field tomography system further includes one or more excitation drivers coupled to the plurality of transducers and configured to generate excitation signals for the plurality of transducers. The soft-field tomography system also includes one or more response detectors coupled to the plurality of transducers and configured to measure a response of the object at the plurality of transducers to the excitation applied by the plurality of transducers based on the excitation signals. The soft-field tomography system additionally includes a soft-field reconstruction module configured to reconstruct a property distribution based on the excitation signals and the measured response.

In accordance with yet another embodiment, a soft-field tomography system is provided that includes a transducer configuration for positioning proximate a surface of an object and spaced along a circumference of the object. The transducer configuration includes a conductive strip having a plurality of measurement regions defined by electrodes surrounded by non-conductive portions. The soft-field tomography system further includes one or more excitation drivers coupled to the plurality of transducers and configured to generate excitation signals for the plurality of transducers. The soft-field tomography system also includes one or more response detectors coupled to the plurality of transducers and configured to measure a response of the object at the plurality of transducers to the excitation applied by the plurality of transducers based on the excitation signals. The soft-field tomography system additionally includes a soft-field reconstruction module configured to reconstruct a property distribution based on the excitation signals and the measured response.

In accordance with still another embodiment, a method for acquiring soft-field data is provided. The method includes applying a plurality of non-uniform excitations to a plurality of transducers of a soft-field tomography system positioned proximate a surface of an object. The excitations are non-uniformly varying in at least one of phase or amplitude. The method also includes measuring a response to the applied excitations at the plurality of transducers and determining a property distribution of the object based on the measured responses.

BRIEF DESCRIPTION OF THE DRAWINGS

The presently disclosed subject matter will be better understood from reading the following description of non-limiting embodiments, with reference to the attached drawings, wherein below.

DETAILED DESCRIPTION

The foregoing summary, as well as the following detailed description of certain embodiments, will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors, controllers, circuits or memories) may be implemented in a single piece of hardware or multiple pieces of hardware. It should be understood that the various embodiments are not limited to the arrangements, component/element interconnections and instrumentality shown in the drawings.

As used herein, a module or step recited in the singular and proceeded with the word "a" or "an" should be understood as not excluding plural of said elements or steps, unless such exclusion is explicitly stated. Furthermore, references to "one embodiment" are not intended to be interpreted as excluding the existence of additional embodiments that also incorporate the recited features. Moreover, unless explicitly stated to the contrary, embodiments "comprising" or "having" a module or a plurality of modules having a particular property may include additional such modules not having that property.

Various embodiments provide transducer configurations and methods for positioning transducers to perform soft-field tomography. For example, the various embodiments provide different positioning arrangements and electrode configurations for measuring the distribution of properties in a multi-material object, such as to estimate the properties of fluids flowing through a pipe. At least one technical effect of various embodiments is improved accuracy and sensitivity without the use of specialized equipment when determining the distribution in multi-material objects, particularly phase-flow through an object having an asymmetric distribution, such as a non-constant or varying flow level that does not encompass the entire inner diameter of the object. For example, in industrial applications, by practicing at least one embodiment, a reconstructed visual representation of a gas distribution flowing within a pipe (that is not completely filled with liquid) may be provided rapidly, such as in real-time while the gas is flowing.

It should be noted that as used herein, "soft-field tomography" refers generally to any tomographic or multidimensional extension of a tomographic method that is not "hard-field tomography".

Figure 1:
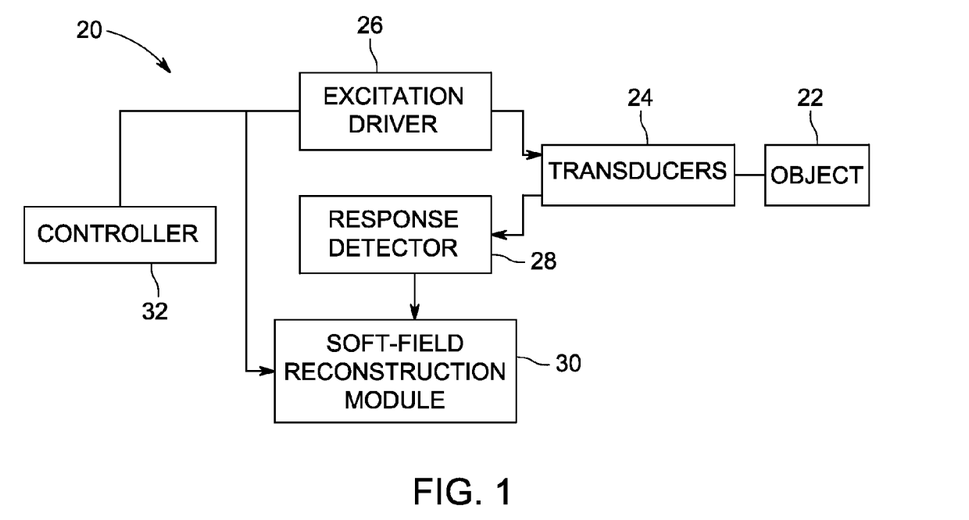
FIG. 1 is a simplified block diagram illustrating a soft-field tomography system formed in accordance with various embodiments.

One embodiment of a soft-field tomography system 20 is illustrated in FIG. 1. For example, the soft-field tomography system 20 may be an Electrical Impedance Tomography (EIT) system used to determine the electrical properties of materials within an object 22, particularly a multi-material object (e.g., illustrated in FIG. 2). In one embodiment, the spatial distribution of electrical conductivity (a) and/or permittivity ($\epsilon$) may be determined inside the object 22 or other area or volume. For example, in one embodiment, the soft-field tomography system 20 provides EIT for multi-phase flow measurements within the object 22, such as the visualization of properties or the volumetric flow rate of gases or oils within petroleum flowing within a pipe.

Figure 2:
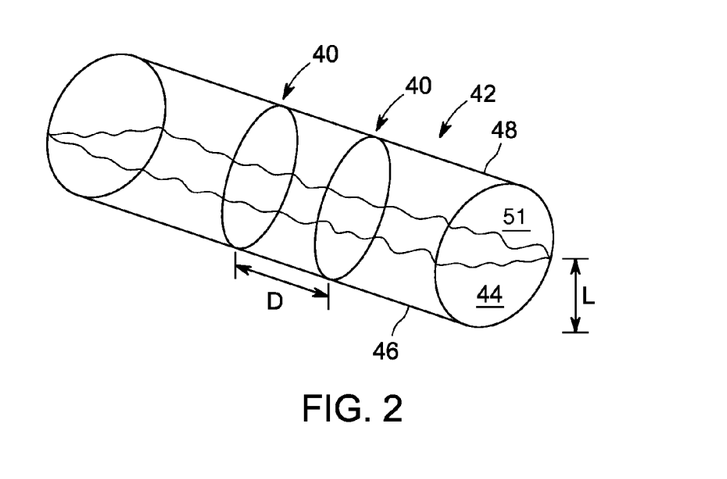
FIG. 2 is a perspective view of a transducer configuration in accordance with one embodiment for soft-field tomography.

In the illustrated embodiment, the system 20 includes a plurality of transducers 24 (e.g., electrodes) that are positioned within or proximate the object, such as spaced around an inner circumference of a generally cylindrical object, for example, a pipe 42, and in contact with at least some of the flowing medium as shown in FIG. 2. In one embodiment, a plurality of rings 40 of transducers 24 is positioned along an inner length, such as spaced apart axially by a distance D (e.g., one meter) along the pipe 42. For example, the transducers 24 (e.g. electrodes) may be positioned on a surface of the inner circumference of the pipe 42, near the surface or penetrating through the surface from outside of the pipe 42 to inside the pipe 42 (e.g., needle electrodes). Thus, the transducers 24 may take different forms, such as surface-contacting electrodes, standoff electrodes, capacitively coupled electrodes, and conducting coils such as antennas, among others. The plurality of rings 40 may be, for example, any structure or combination of elements that generally form a circular or other elliptical shape (or other shape), such as a plurality of transducers 24 arranged or supported on a structure extending 360 degrees. However, the transducers 24 may extend along less than the complete 360 degrees.

The spaced apart rings 40 may form a multi-phase flow meter in accordance with various embodiments to determine, for example, how much gas is in the pipe 42 (based on a visualization of gas and oil in the pipe 42) and the flow velocity based on a differential measurement between the rings 40 (at two locations in the pipe 42). Thus, in accordance with various embodiments, a reconstruction is performed based on signals received at each of the rings 40. Accordingly, a volume visualization of a gas property distribution or a determination of gas flow in the pipe 42 may be provided, such as to determine the amount of gas and oil flowing therethrough. In some embodiments, additional or fewer rings 40 may be provided.

It should be noted that the soft-field tomography system 20 may be other types of systems. For example, the soft-field tomography system 20 may be an Electrical Impedance Spectroscopy (EIS) system, an Electrical Resistance Tomography (ERT) system or an Electrical Capacitance Tomography (ECT) system, among others that use different types of excitations or patterns.

An excitation driver 26 and a response detector 28 are coupled to the transducers 24, which are each connected to a soft-field reconstruction module 30. The soft-field reconstruction module 30 may be any type of processor or computing device that performs soft-field reconstruction based at least in part on received responses from the transducers 24 as described in more detail herein. For example, the soft-field reconstruction module 30 may be hardware, software or a combination thereof. In one embodiment, the excitation driver 26 and the response detector 28 are physically separate devices. In other embodiments, the excitation driver 26 and the response detector 28 are physically integrated as one element. A controller 32 is also provided and sends instructions to the excitation driver 26 that drives the transducers 24 based on the instructions. It should be noted that the excitation driver 26 may be provided in connection with all or a subset of transducers 24. Additionally, the response detectors 28 may be coupled directly or indirectly to the transducers 24.

It also should be noted that different types of excitations may be used to obtain property distribution data for use in the reconstruction process of the various embodiments. For example, different types of electrical signals, among others, may be used in combination with the various embodiments. In these different embodiments, the transducers 24 may be coupled to the object 22 in different ways and not necessarily in direct contact or only at an inner surface of the object 22 (e.g., coupled electrically, capacitively, galvanically, etc.).

In some embodiments, the soft-field tomography system 20 can be used for generating a visual representation of the electrical impedance distribution in a variety of applications, such as for determining the material properties in a mixed fluid flow including oil and water (or other fluids or gases, such as petroleum), or for an underground earth area for soil analysis and roadbed inspection, among others. However, the embodiments may be applied to other applications, such as where the object 22 is a human body region, such as a head, a chest, or a leg, wherein air and tissue have different electrical conductivities.

In various embodiments, the transducers 24 are formed from any suitable material. For example, the types of transducer 24 used may be based on the particular application, such that a corresponding transducer type (e.g., electrode, coil, etc.) is used to generate the soft-field excitations (e.g., electromagnetic (EM) field) and receive responses of the object 22 to the excitations for the particular application. In some embodiments, a conductive material may be used to establish electrical current. For example, the transducers 24 may be formed from one or more metals such as copper, gold, platinum, steel, silver, and alloys thereof. Other exemplary materials for forming the transducers 24 include non-metals that are electrically conductive, such as a silicon based materials used in combination with micro-circuits. In one embodiment, where the object 22 is the pipe 42 with gas or fluid flowing therethrough, the transducers 24 are formed to be liquid proof.

Additionally, the transducers 24 may be formed in different shapes and/or sizes, for example, as rod shaped, flat plate shaped, needle shaped or diamond shaped structures, among others, as described in detail herein. It should be noted that in some embodiments, the transducers 24 are insulated from one another. In other embodiments, the transducers 24 can be positioned in direct ohmic contact with the object 22 or may be capacitively coupled to the object 22.

In operation, the transducers 24 or a subset of the transducers 24 may be used to transmit signals (e.g., deliver or modulate signals), for example, deliver electrical current continuously or to deliver a time-varying signal such that excitations may be applied across a temporal frequency range (e.g., 1 kHz to 1 MHz) to generate an EM field within the object 22. In an EIT application, the resulting surface potentials, namely the voltages on the transducers 24 are measured to determine an electrical conductivity or permittivity distribution using reconstruction methods as described herein. For example, a visual distribution may be reconstructed based on the geometry of the transducers 24, the applied currents and the measured voltages.

Thus, in various embodiments, the excitation driver 26 applies an excitation to each of the transducers 24 and the response detector 28 measures a response on each of the transducers 24 (which may be multiplexed by a multiplexer) in response to the excitation applied on the transducers 24. It should be noted that any type of excitation may be provided, for example, electrical current or electrical voltage, among others.

Figure 3:
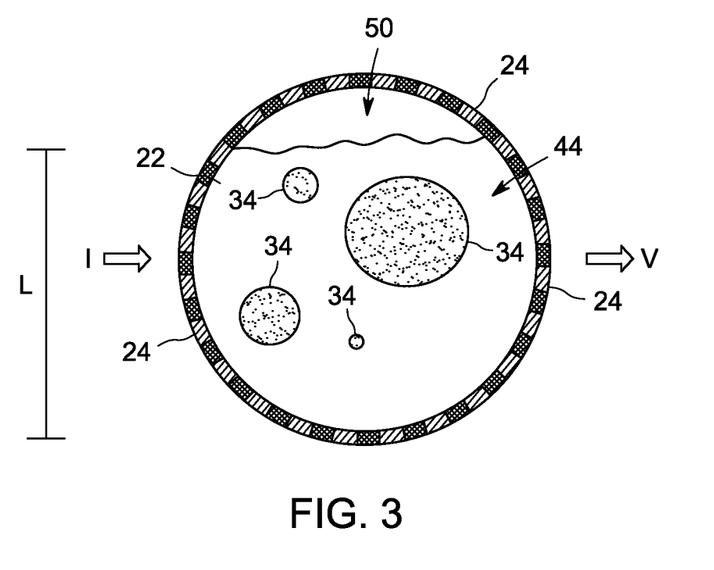
FIG. 3 is a simplified diagram illustrating reconstruction of a property distribution.

For example, in an EIT application, and as illustrated in FIG. 3, a soft-field reconstruction is performed to identify regions of interest 34 (e.g., gas bubbles within a flowing fluid) within the object 22. As shown, the response detector 28 (shown in FIG. 1) measures a response voltage (or a response current) on the transducers 24 in response to the current (or voltage) applied by the excitation driver 26 (shown in FIG. 1) to the transducers 24.

It should be noted that the response detector 28 also may include one or more analog-signal-conditioning elements (not shown) that amplifies and/or filters the measured response voltage or current. In other embodiments, a processor of the soft-field tomography system 20 includes a signal conditioning element for amplifying and/or filtering the response voltage or response current received from the response detector 28.

The soft-field reconstruction module 30, thus, computes a response of the object 22 to the applied excitation. Accordingly, the soft-field tomography system 20 may be used for reconstruction of a property distribution or flow visualization.

As can be seen in FIGS. 2 and 3, when measuring fluid flow through the pipe 42, for example, a horizontally oriented pipe (or any non-vertically oriented pipe), the level of the fluid 44 therein may not encompass the entire inner circumference of the pipe 42 from a bottom 46 to a top 48 of the pipe 42. For example, the level of the fluid 44 therein may vary based on the fluid flow rate or amount of fluid flowing therethrough and defines a fluid flow path. As shown, the fluid 44 in the pipe 42 generally settles toward the bottom 46 of the pipe 42 due to gravity, such that the fluid flow part is less than the entire inner region of the pipe 42. This settling of the fluid 44 can occur in any pipe 42, for example, any pipe 42 that is not vertical. Thus, a level of the fluid 44 (as indicated by L in FIGS. 2 and 3) results in a portion 51 of the pipe 42 that does not have fluid 44 flowing therethrough (namely a non-fluid flow path) and accordingly is not in contact with the some of the transducers 24, in particular, toward the top 48 of the pipe 42. The portion 51 generally defines a space, for example, an air space having no fluid flowing along that region. It should be noted that the bottom 46 of the pipe 42 in various embodiments generally refers to that portion of the pipe 42 wherein the fluid 44 flows due to gravity, such that the fluid 44 extends from the bottom 46 of the pipe 42 upward.

Various embodiments provide configurations and arrangements of transducers 24 for use in flow measurements and property distribution determinations for objects in a non-vertical orientation, such as a horizontally oriented pipe or objects that are not symmetrically shaped (e.g., a human torso or head). However, it should be noted that the various embodiments may be used in connection with any object in any orientation between horizontal and vertical, as well as for vertically oriented objects or object having different asymmetries.

Figure 4:
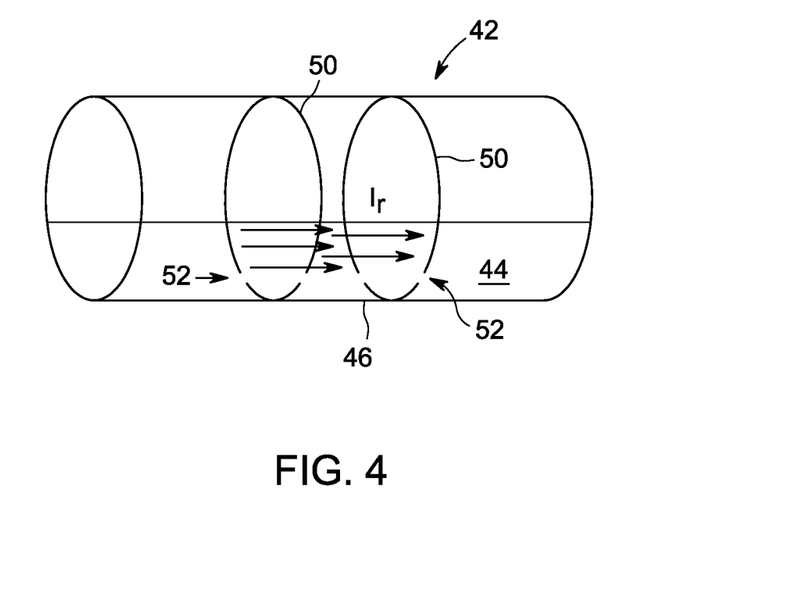
FIG. 4 is a diagram of a transducer configuration in accordance with other various embodiments for soft-field tomography.
Figure 5:
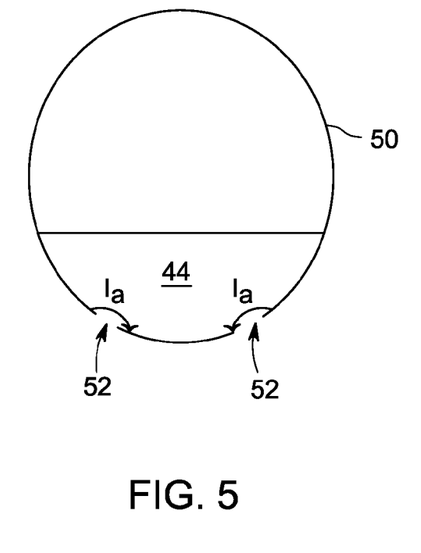
FIG. 5 is a simplified diagram of a transducer ring in accordance with one embodiment that may be implemented as the transducer configuration of FIG. 4.

In one embodiment, as illustrated in FIGS. 4 and 5, the transducers 24 are defined by circular rings 50 spaced apart along the inner surface of the pipe 42. For example, in one embodiment, the rings 50 are formed from metal bands or strips (e.g., copper or steel bands) to define conductive rings. In general, the rings 50 may be any type of electrically conductive ring. It should be noted that although two rings 50 are shown, additional or fewer rings 50 may be used. Additionally, the spacing between the rings 50 may be varied as desired or needed, for example, based on the application or the maximum rate of fluid flow through the pipe 42, among others. Also, the thickness and width of the rings 50 likewise may be varied.

In one embodiment, one or more of the rings 50 include one or more discontinuities (two are shown) that define non-conductive portions or regions or electrical discontinuities, illustrated as gaps 52 in the structure of the rings 50. Thus, in this embodiment, the rings 50 are not continuous around the entire inner circumference of the pipe 42. The rings 50 may be positioned and coupled within the pipe 42 such that the gaps 52 are located toward the bottom 46 of the pipe 42. For example, the gaps 52 may be located within the bottom forty-five degrees relative to horizontal. The gaps 52 are generally located along the bottom half of the pipe 42 in some embodiments to be in continuous contact with the fluid in the pipe 42. However, the location and positioning of the gaps 52 again may be varied as desired or needed. Additionally, in some embodiments, the gaps 52 may be provided in the top half of the pipe 42.

Figure 6:
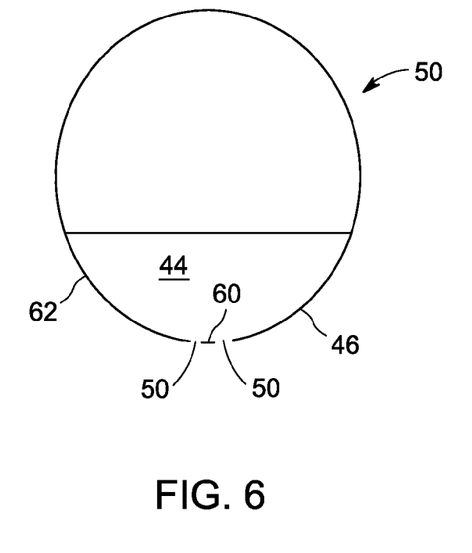
FIG. 6 is a simplified diagram of a transducer ring in accordance with another embodiment that may be implemented as the transducer configuration of FIG. 4.

The gaps 52 may be formed to be any discontinuity in the rings 50, and in some embodiments, may be notched out from the sings 50. In other embodiments, the gaps 52 include non-electrically conductive material therein. In one embodiment, as shown in FIG. 6, the gaps 52 are located generally at the bottom of the rings 50, namely adjacent the bottom 46 of the pipe 42. For example, in one embodiment, the rings 50 are formed from metal, that extend 358° with the remaining two degrees (2°) filled with a metal arc 60 (or any type of conductive arc portion), which may encompass about 1° and having the gaps 52 on each side thereof that each encompass about 0.5° of the rings 50. It should be noted that the gaps 52 in various embodiments are formed from any suitable electrically insulating material that provides an electrical short therebetween. However, in some embodiments, the gaps 52 may be air gaps.

Thus, the rings 50 in some embodiments have a minor arc defined by the metal arc 60 and a major arc 62 defined by the remaining metal portion of the rings 50. In various embodiments, different conductivity or impedance measurements may be performed using the rings 50. For example, in one embodiment, an inter-ring conduction measurement and an intra-ring conduction measurement are both performed. In particular, the inter-ring conduction measurement includes measuring the impedance between the rings 50 as illustrated by the arrows Ir in FIG. 4. The intra-ring conduction measurement includes measuring the impedance between the major arc 62 and the minor arc 60 as illustrated by the arrows Ia in FIG. 5. The measurements may be performed using the soft-field tomography system 20 (shown in FIG. 1).

The inter-ring conduction measurement may be used, for example, for phase fraction estimation during the soft-field reconstruction of the property distribution. The intra-ring conduction measurement may be used, for example, for liquid property estimation during the soft-field reconstruction of the property distribution. It should be noted that the soft-field reconstruction may be performed using any suitable reconstruction method, for example, any suitable EIT reconstruction method. In one embodiment, the property distribution of liquid and gas flowing the through the pipe 42 may be determined by measuring the impedance between the two rings 50 and normalizing this measurement, such as, by, dividing this impedance by the measured impedance between the major arc 62 and the minor arc 60. Using these measurements, the distribution of liquid and gas flowing through the pipe 42 may be determined using any suitable soft-field reconstruction. Thus, the distribution and flow of a fluid through the pipe 42, which may include gas, liquid, sand, etc. may be determined using different conduction measurements as described above. Accordingly, the level of flow through the pipe 42 and the properties thereof may be determined using an electrical current applied to the rings 50, for example, two measurement rings spaced apart along the pipe 42 or other object.

Figure 7:
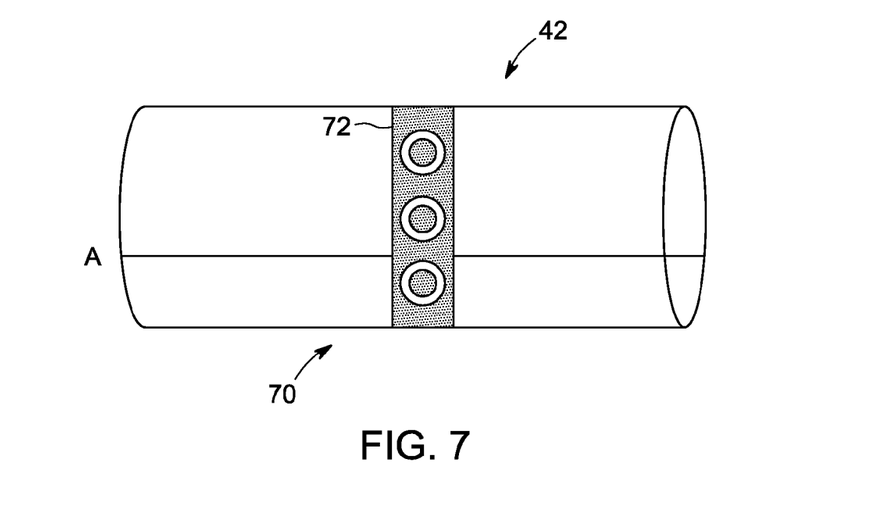
FIG. 7 is a simplified diagram of a ring of transducers in connection with a cylindrical object.
Figure 8:
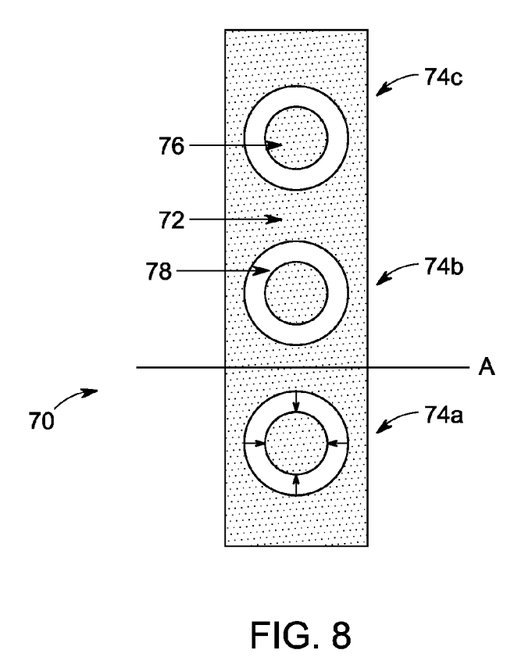
FIG. 8 is a diagram of a portion of the ring of FIG. 7.

In another embodiment, as shown in FIGS. 7 and 8, a transducer configuration 70 may be provided that is formed as a ring 72 defined by a conductive band or strip (e.g., copper or steel bands) that extends around the inner circumference of the pipe 42. In this embodiment, a single ring 72 may be used. The ring 72 includes a plurality of measurement regions 74 defined by circular electrodes 76 surrounded by non-conductive rings portions, illustrated as gaps 78. It should be noted that the gaps 78 in various embodiments are formed from any suitable electrically insulating material such that an electrical short is provided therebetween. However, in some embodiments, the gaps 78 may be air gaps. Thus, the gap 78 generally defines a non-conductive ring around the electrode 76.

It also should be noted that although the measurement regions 74 are shown as equally spaced around the ring 72, an unequal or random spacing may be provided as described in more detail herein. It further should be noted that although the electrodes 76 are generally circular in shape, the electrodes 76 may have different shapes as also described in more detail herein.

In one embodiment, excitations, for example, electrical current is applied to the electrodes 76 by the excitation driver 26 (shown in FIG. 1) and the ring 72 is electrically grounded. Accordingly, electrical flow is from the electrodes 76 to the ring 72, such as when the particular measurement region 74 is immersed in or in contact with a fluid as conduction results if fluid is present, but not if fluid is not present. In operation, by determining the measurement regions 74 that are conducting, a determination can be made as to the level of the fluid within the pipe 42. For example, if the fluid is at a level as indicated by the line A in FIGS. 7 and 8, the measurement region 74a has a conducting electrode 76. Additionally, background conductivity may be measured with the electrodes 76 to thereby determine a distribution of gas within the fluid within the pipe 42 using soft-field image reconstruction techniques.

Figure 9:
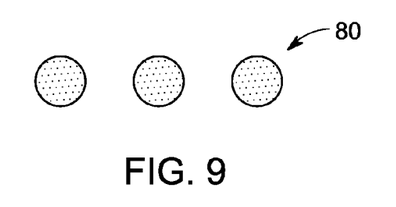
FIG. 9 is a diagram illustrating electrodes having a shape in accordance one embodiment.
Figure 10:
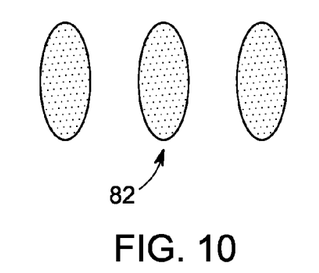
FIG. 10 is a diagram illustrating electrodes having a shape in accordance with another embodiment.

The transducers 24 in various embodiments may have different shapes or arrangements. For example, the transducers 24 may be formed from generally circular electrodes 80 as shown in FIG. 9 or elliptical (or oval) electrode 82 as shown in FIG. 10. The number and spacing of the electrodes is shown for illustration only.

Figure 11:
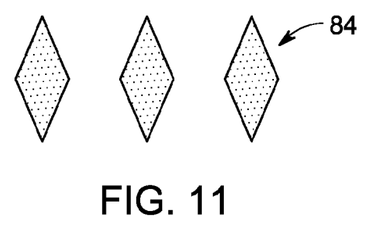
FIG. 11 is a diagram illustrating electrodes having a shape in accordance with another embodiment.
Figure 12:
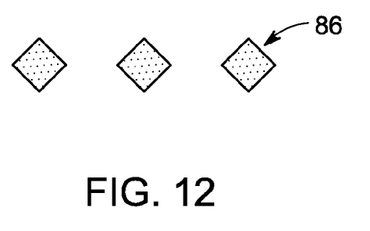
FIG. 12 is a diagram illustrating electrodes having a shape in accordance with another embodiment.

In other embodiments, for example, the transducers 24 may be formed from diamond shaped electrodes 84 as shown in FIG. 11, which are illustrated as rhomboidal shaped. In another embodiment, as shown in FIG. 12, the transducers 24 are formed from diamond shaped electrodes 86 that have a square shape that is rotated to form the diamond.

Figure 13:
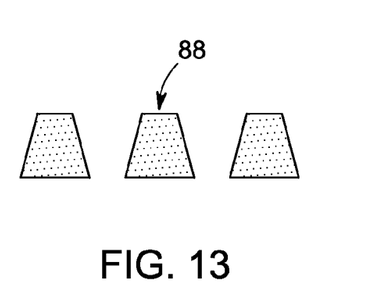
FIG. 13 is a diagram illustrating electrodes having a shape in accordance with another embodiment.
Figure 14:
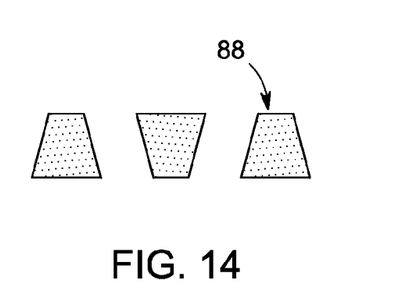
FIG. 14 is a diagram illustrating the electrodes of FIG. 13 in a different configuration.

As shown in FIGS. 13 and 14, the transducers 24 may be formed from trapezoidal shaped electrodes 88 that may be arranged in different patterns. For example, as shown in FIG. 13, the trapezoidal shaped electrodes 88 are aligned such that the longer and shorter parallel sides of the trapezoidal shaped electrodes 88 are pointed in the same direction. However, the longer and shorter parallel sides of the trapezoidal shaped electrodes 88 may be pointed in different directions as shown in FIG. 14. It should be noted that alternating ones of the trapezoidal shaped electrodes 88 may be rotated 180° or other patterns or orientations may be used.

Figure 15:
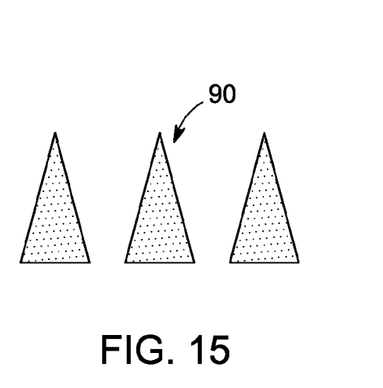
FIG. 15 is a diagram illustrating electrodes having a shape in accordance with another embodiment.
Figure 16:
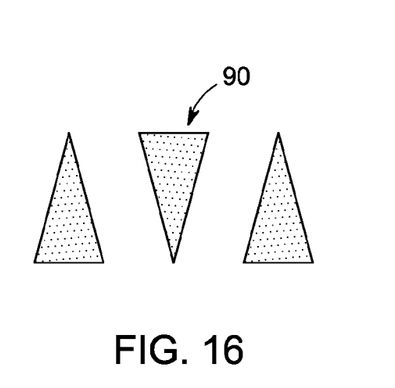
FIG. 16 is a diagram illustrating the electrodes of FIG. 15 in a different configuration.

As shown in FIGS. 15 and 16, the transducers 24 may be formed from triangular shaped electrodes 90 that may be arranged in different patterns. For example, as shown in FIG. 15, the triangular shaped electrodes 90 (e.g., isosceles triangles) are aligned such that the apex of the triangular shaped electrodes 90 are pointed in the same direction. However, the apex of the triangular shaped electrodes 90 may be pointed in different directions as shown in FIG. 16. It should be noted that alternating ones of the triangular shaped electrodes 90 may be rotated 180° or other patterns or orientations may be used. It also should be noted that although isosceles triangles are shown, the triangular shaped electrodes 90 may be formed in equilateral triangle or scalene triangle shapes. Some of the different shapes may result in reduced cross-talk between the transducers 24.

Figure 17:
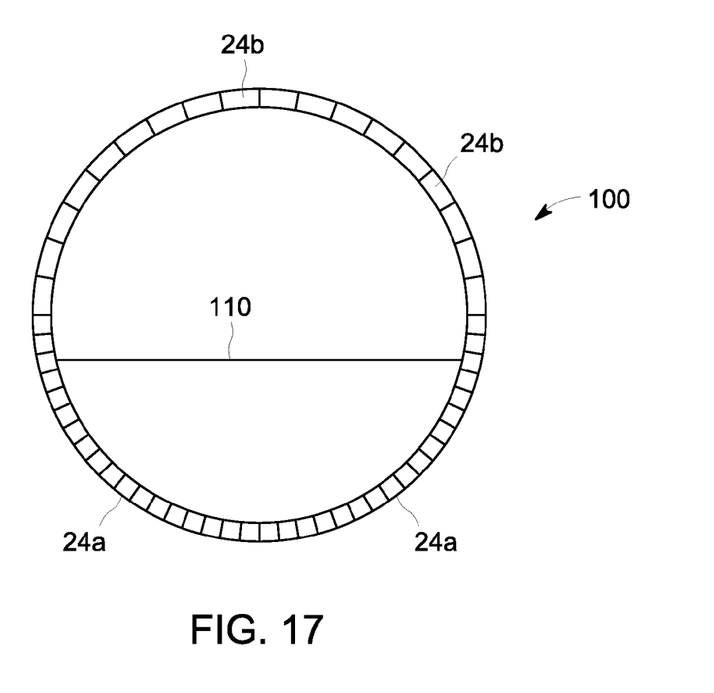
FIG. 17 is a diagram illustrating transducers asymmetrically distributed in accordance with one embodiment.

Other variations and modifications are contemplated. For example, the transducers 24 may be asymmetrically provided, such as asymmetrically distributed within a measurement region. The asymmetrical arrangement of transducers 24 also may be combined with other embodiments described herein. For example, as shown in FIG. 17, in one embodiment, transducers 24 forming a measurement ring 100 are unequally sized. In this embodiment, a subset of the transducers 24, namely the transducers 24*a* provided along a lower portion of the ring 100 are dimensionally smaller (e.g., shorter or narrower) than another subset of the transducers 24, namely the transducers 24*b* provided along an upper portion of the ring 100. It should be noted that the different sized transducers 24*a* and 24*b* may be positioned along more or less of the ring 100 than shown in FIG. 17. For example, the transducers 24*a* may extend further or less along the ring 100.

As illustrated in FIG. 17, in general, the smaller sized transducers 24*a*, allow more transducers 24*a* to be positioned along a portion of the ring 100 that is more likely to come into contact with a fluid (e.g., within a fluid flow path). Thus, in one embodiment, the transducers 24*a* are positioned towards the bottom of the pipe 42 (shown, for example, in FIG. 2), such as generally below a fluid level 110. However, as should be appreciated, the fluid level 110 may rise or fall.

It should be noted that the transducers 24 in some embodiments may gradually or incrementally increase or decrease in size along the ring 100. Thus, more than two different sizes of transducers 24 (as shown in FIG. 17) may be used.

Figure 18:
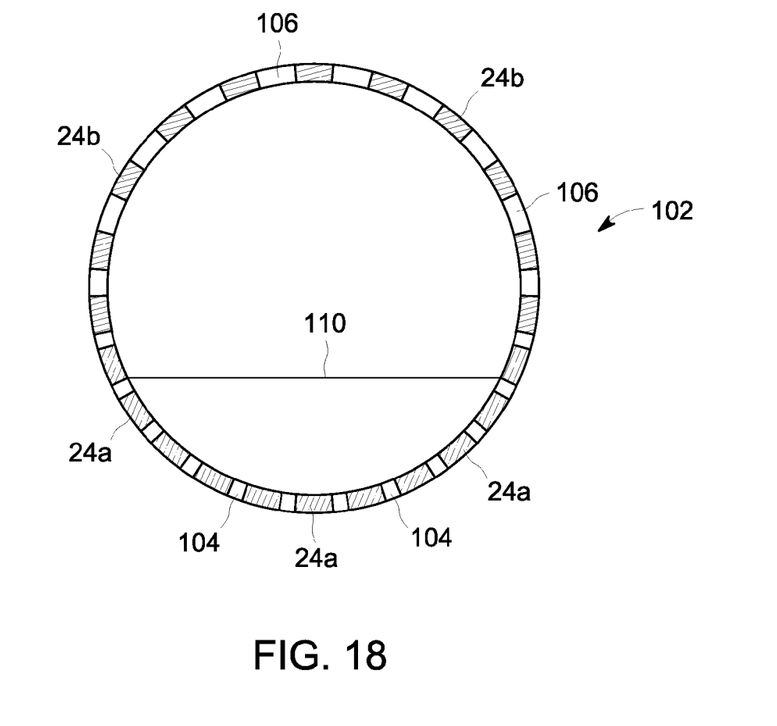
FIG. 18 is a diagram illustrating transducers asymmetrically distributed in accordance with another embodiment.

In other embodiments, the transducers 24 may be unequally spaced along a measurement ring 102 as shown in FIG. 18. In this embodiment, the transducers 24*a* provided along a lower portion of the ring 100 are spaced closer together (e.g., smaller gap 104 between adjacent transducers 24*a*) that the transducers 24*b* provided along an upper portion of the ring 100 having gaps 106. It should be noted that the different spaced transducers 24*a* and 24*b* may be positioned along more or less of the ring 100 than shown in FIG. 18. For example, the spacing for transducers 24*a* may extend further or less along the ring 100.

As illustrated in FIG. 18, in general, the closer spaced transducers 24*a*, allow more transducers 24*a* to be positioned along a portion of the ring 102 that is more likely to come into contact with a fluid (e.g., within a fluid flow path). Thus, in one embodiment, the transducers 24*a* are positioned towards the bottom of the pipe 42 (shown, for example, in FIG. 2), such as generally below a fluid level 110. However, as should again be appreciated, the fluid level 110 may rise or fall.

It should be noted that the spacing between transducers 24 in some embodiments may gradually or incrementally increase or decrease in along the ring 102. Thus, more than two different spacing widths of transducers 24 (as shown in FIG. 18) may be used. Additionally, the transducers 24 may be sized the same or unequally as described above.

It also should be noted that although the transducers 24 are shown as forming part of a ring structure, the transducers 24 may be separately coupled to the pipe 42 or other structure. Thus, the transducers 24 may be provided as part of a single combined structure or supporting element including all of the transducers 24 or some of the transducers 24, or may be separately provided.

Thus, in various embodiments, more transducers 24 are positioned along at least one portion the pipe 42 having a smaller diameter, such as at the bottom 46 of the pipe 42 instead of at the middle or at the top 48. Accordingly, the sensitivity of the measurements by the soft-field tomography system 20 may be changed. The relative number or density of the transducers 24 may be changed in different ways in addition to changing the size and spacing of the transducers 24. For example, the shape or orientation of the transducers 24 may be changed.

Figure 19:
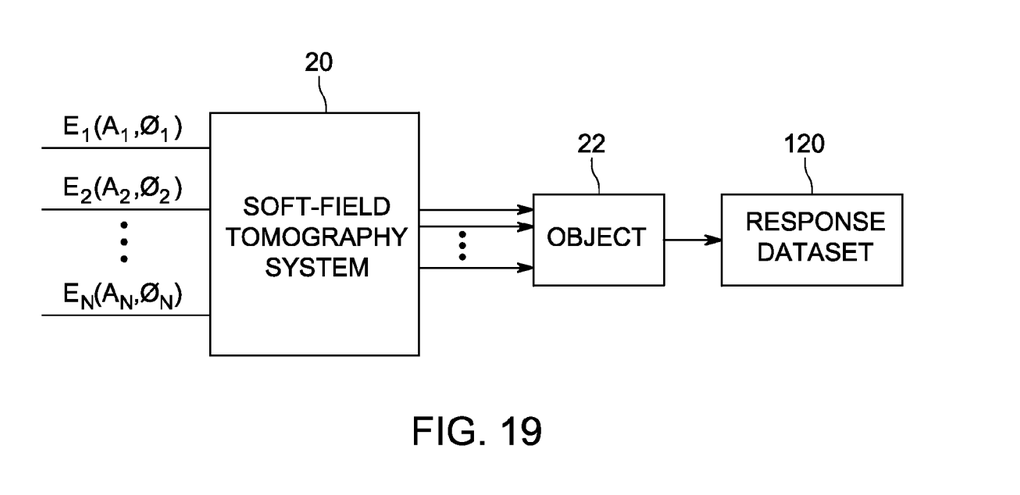
FIG. 19 is a simplified block diagram illustrating excitation signal generation and data acquisition in accordance with one embodiment.

In various embodiments, different excitation patterns (e.g., trigonometric patterns) may be generated, particularly in the asymmetric distribution arrangement (e.g., asymmetric electrode placement). For example, one or more optimized patterns may be generated that optimizes the excitation pattern for a particular object geometry, electrode distribution or type of excitation. In particular, in one embodiment as shown in FIG. 19, the soft-field tomography system 20 generates excitations at the transducers 24, which may be excitation currents that having varying phase or amplitude, which may be phase modulated and/or amplitude modulated wherein phase and/or amplitude variance is non-uniform in spacing between at least some of the transducers 24. For example, non-uniformly spaced phase modulated and/or amplitude modulated excitations may be applied to the plurality of the transducers 24 to generate a field within the object 22 (shown in FIGS. 1 and 2) that may rotate spatially and temporally. In various embodiments, the frequency of the excitations is the same for all of the transducers 24. It should be noted that the excitations may be applied over time at each of the transducers 24 or at the same time.

In particular, at a first excitation time $T_1$, an n-phase modulated excitation (which optionally may be amplitude modulated) or an n-amplitude modulated excitation is applied to a set of N transducers 24, where N is greater than one and the modulation is non-uniform between at least a subset of the transducers 24. Thereafter, at one or more excitation times $T_2 \ldots T_N$, an n-phase modulated (or phase and amplitude modulated) or amplitude modulated excitation is applied to a set of N transducers 24 (e.g., a different set of transducers 24) until n-phase modulated (or phase and amplitude modulated) excitations are applied to all of the transducers 24. Thus, in various embodiments, a plurality of excitation patterns are applied with all or a subset of the transducers 24 excited simultaneously. In particular, an excitation pattern is applied to all or a subset of the transducers 24 that is non-uniformly spaced in phase, amplitude or phase and amplitude.

Thus, as illustrated in FIG. 19, after a first excitation sequence, which may occur over multiple excitation times, a non-uniformly spaced excitation is applied to all or a subset of the transducers 24. In particular, excitation $E_1(A_1, \Phi_1)$ is applied to transducer 1, excitation $E_2(A_2, \Phi_2)$ is applied to transducer 2 . . . excitation $E_N(A_N, \Phi_N)$ is applied to transducer N, where the phase (or angle) $\Phi$ is varied and/or the amplitude A is varied such that the phase and/or amplitude is varied between at least a subset of the transducers 24 such that variance between at least some of the transducers 24 is different (e.g., not the same change in phase and/or amplitude between excitations for different transducers 24). Thus, instead of having, for example, excitations applied to the transducers having uniformly spaced phases of 0°, 90°, 180° and 270°, the spacing or change in phase varies, such as based on the relative spacing between the transducers 24 or the size of the transducers 24. However, the excitations applied to at least some of transducers 24 may be uniform. For example, the excitations applied to the transducers 24 toward the bottom of the rings 100 and 102 (shown in FIGS. 17 and 18) do not have excitations applied thereto with the same phase and/or amplitude difference between adjacent transducers 24 as the transducers 24 toward the top of the rings 100 or 102, where the spacing or size of the transducer is different.

Thus, the difference in phase and/or amplitude of the excitations applied to different transducers 24 may be varied based on, for example, the spacing between the transducers 24, the size of the transducers 24 and/or the shape of the transducers 24. For example, in one embodiment, the phase difference between excitations applied to a set of the transducers 24 is 10° (e.g., 0°, 10°, 20°, 30° . . . ) and the phase difference between excitations applied to a different set of the transducers 24 is 45° (e.g., 0°, 45°, 90°, 135° . . . ) or 90° (e.g., 0°, 90°, 180° and 270).

After an excitation sequence has been performed, each of the transducers 24 has an excitation applied thereto wherein the difference in phase and/or amplitude between some of the excitations is non-uniform. Thus, in one example, the excitation applied to each of the transducers 24 is a signal having the same varying amplitude A, namely that the magnitude of the amplitude varies the same, but having a different phase Φ, wherein the difference in phase for the excitations applied to the transducers is varied or non-uniform for different subsets of the transducers 24. However, in other embodiments the amplitude and difference also varies.

A response is measured at all of the transducers 24 after application of each of the excitations, namely after each of the excitations during an excitation sequence, which may be applied to different subsets of the transducers 24. For example, if all of the transducers 24 are excited at two different excitation times that define a single excitation sequence, first and second responses are measured after the application of the first and second excitation times ($t_1$ and $t_2$) to generate a response data set 120. The first and second excitations, thus, are excitations that generate an EM field that rotates spatially and/or temporally. The multiple responses may be analyzed or combined to reconstruct the distribution of different materials. For example, the responses in the response data set 120 may be combined using any suitable combination process, such as an additive or scaling process, among others.

It should be noted that in various embodiments, a feedback path optionally may be provided from the response to the excitation. For example, the response dataset 120 may be used as feedback to the soft-filed tomography system 20. In some embodiments, the excitation is also modified or altered according to the measurements.

Figure 20:
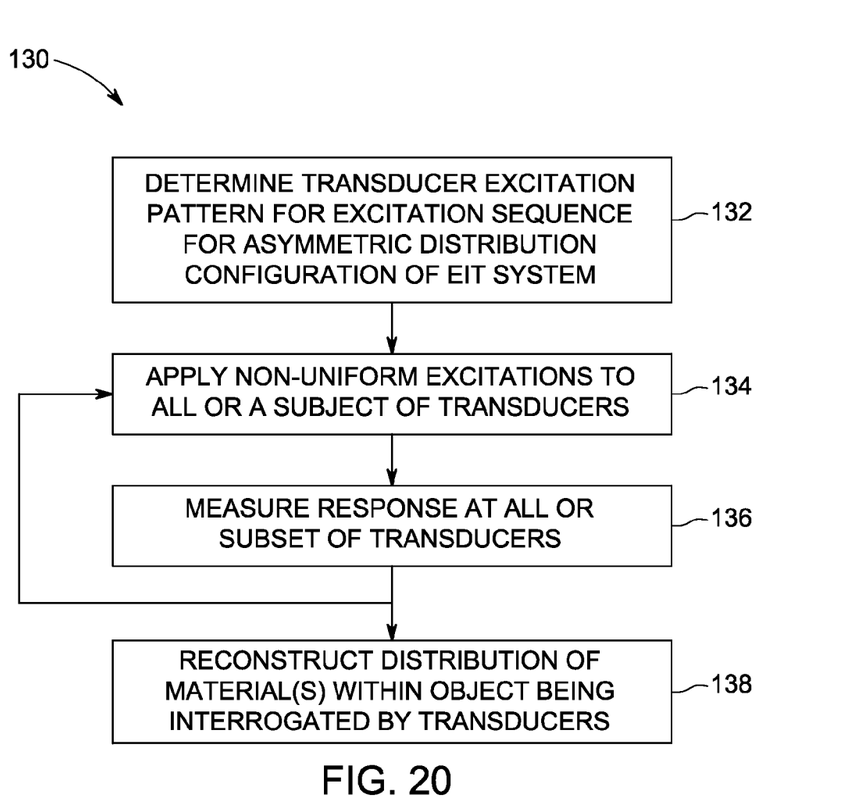
FIG. 20 is a flowchart of a method to generate excitations for asymmetrically arranged transducers of a soft-field tomography system in accordance with various embodiments.

In various embodiments, a method 130 as illustrated in FIG. 20 is provided to generate excitations for transducers of a soft-field tomography system, such as the transducers 24. The method 130 may be implemented in connection with a soft-field tomography system that includes several transducers (e.g., electrodes) that are asymmetrically positioned or distributed around an object. The method 130 includes determining at 132 a transducer excitation pattern for an excitation sequence to be used to interrogate an object using the transducers. For example, a determination may be made based on the type of material properties to be determined, the type of object to be examined/interrogated, etc., the particular transducers or sets of transducers to be excited, including the positioning, spacing between, size and/or shape of the transducers, or the pattern or order or excitation, among others. In one embodiment, the selection of "N" transducers or sets of transducers to excite is based on a logic implementation, which may be based on the intended application and system requirements, such that resolution, data acquisition, noise performance (e.g., signal-to-noise ratio), detection capability, complexity or acquisition speed is optimized or improved, while reducing or minimizing the required analysis in determining the materials/compositions. In another embodiment, the selection of "N" transducers or sets of transducers to excite is based on an optimization using, for example, signal-to-noise ratio, instrumentation complexity and acquisition speed, which may be application dependent.

Thereafter, excitations are applied to all or a subset of transducers at 134. In some embodiments, the excitations may be applied to all of the transducers. As one example, at a first excitation time of an excitation sequence, a set of "N" electrodes is supplied with excitations having a phase and/or amplitude difference (which are non-uniform among at least two subsets of transducers), for example, electrical signals (e.g., voltage or current) distributed in space (symmetrically or asymmetrically in space and time). As the excitations are applied, the responses (e.g., resulting voltage or current signals) through or at all of a subset of the "N" transducers are measured at 136.

It should be noted that steps 134 and 136 are optionally repeated until all derived excitation patterns are applied to all or a subset of the transducers and responses measured. Thus, this process is continued until excitations have been applied to all of the transducers at least once.

Once all of the transducers have been provided with an excitation signal, thereby completing the excitation sequence, a distribution of the material(s) within the object being interrogated by the transducers is reconstructed at 138. For example, any suitable EIS/EIT reconstruction technique may be used.

As one example, and in one embodiment, non-uniform phase and/or amplitude electrical impedance tomography for an asymmetric distribution application may be performed using the various embodiments in connection with multi-phase or multi-material flow measurement and property distribution determinations. For example, EIT in accordance with various embodiments may be performed where the presence of a foreign material is to be detected real-time across the cross-section of the body, such as flow sensing applications, mold filling visualization in casting, chemical and other process engineering applications. As another example, the various embodiments may be used in inspection applications where the presence of a foreign material or loss of material is to be detected across the cross-section of piece under inspection. Some examples of applications include the inspection of composites, the inspection of metals (e.g., welds, etc.), polymers, material loss along a thickness of a pipe, etc.

As still another example, the various embodiments may be used for various medical or bio-medical applications, such as monitoring of lung function, detection of cancer in the skin and breast and location of epileptic foci, among others. In these embodiments, the asymmetric distribution can result from the non-symmetrical shape of the patient, such as during a cranial or thoracic exam.

The various embodiments and/or components, for example, the modules, elements, or components and controllers therein, also may be implemented as part of one or more computers or processors. The computer or processor may include a computing device, an input device, a display unit and an interface, for example, for accessing the Internet. The computer or processor may include a microprocessor. The microprocessor may be connected to a communication bus. The computer or processor may also include a memory. The memory may include Random Access Memory (RAM) and Read Only Memory (ROM). The computer or processor further may include a storage device, which may be a hard disk drive or a removable storage drive such as an optical disk drive, solid state disk drive (e.g., flash RAM), and the like. The storage device may also be other similar means for loading computer programs or other instructions into the computer or processor.

As used herein, the term "computer" or "module" may include any processor-based or microprocessor-based system including systems using microcontrollers, reduced instruction set computers (RISC), application specific integrated circuits (ASICs), field-programmable gate arrays (FPGAs), graphical processing units (CPUs), logic circuits, and any other circuit or processor capable of executing the functions described herein. The above examples are exemplary only, and are thus not intended to limit in any way the definition and/or meaning of the term "computer".

The computer or processor executes a set of instructions that are stored in one or more storage elements, in order to process input data. The storage elements may also store data or other information as desired or needed. The storage element may be in the form of an information source or a physical memory element within a processing machine.

The set of instructions may include various commands that instruct the computer or processor as a processing machine to perform specific operations such as the methods and processes of the various embodiments. The set of instructions may be in the form of a software program, which may form part of a tangible non-transitory computer readable medium or media. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to operator commands, or in response to results of previous processing, or in response to a request made by another processing machine.

As used herein, the terms "software", "firmware" and "algorithm" are interchangeable, and include any computer program stored in memory for execution by a computer, including RAM memory, ROM memory, EPROM memory, EEPROM memory, and non-volatile RAM (NVRAM) memory. The above memory types are exemplary only, and are thus not limiting as to the types of memory usable for storage of a computer program.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the various embodiments without departing therefrom. While the dimensions and types of materials described herein are intended to define the parameters of the various embodiments, the embodiments are by no means limiting and are exemplary embodiments. Many other embodiments will be apparent to those of skill in the art upon reviewing the above description. The scope of the various embodiments should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. §112, sixth paragraph, unless and until such claim limitations expressly use the phrase "means for" followed by a statement of function void of further structure.

This written description uses examples to disclose the various embodiments, including the best mode, and also to enable any person skilled in the art to practice the various embodiments, including making and using any devices or systems and performing any incorporated methods. The patentable scope of the various embodiments is defined by the claims, and may include other examples that occur to those skilled in the art. Such other examples are intended to be within the scope of the claims if the examples have structural elements that do not differ from the literal language of the claims, or if the examples include equivalent structural elements with insubstantial differences from the literal languages of the claims.

What is claimed is:

1. A soft-field tomography system comprising:
a plurality of transducers configured for positioning proximate a surface of an object and spaced apart along the object, at least one of the transducers being formed from at least one conductive ring that extends around the object, the at least one conductive ring including a discontinuity that defines a non-conductive portion, wherein the at least one conductive ring includes a continuous portion that extends around at least one-half of a circumference of the object;
one or more excitation drivers coupled to the plurality of transducers and configured to generate excitation signals for the plurality of transducers;
one or more response detectors coupled to the plurality of transducers and configured to measure a response of the object at the plurality of transducers to the excitation applied by the plurality of transducers based on the excitation signals; and
a soft-field reconstruction module configured to reconstruct a property distribution based on the excitation signals and the measured response.

2. The soft-field tomography system of claim 1, wherein the discontinuity in the at least one conductive ring defining the non-conductive portion is positioned at a bottom of the rings within a fluid flow path.

3. The soft-field tomography system of claim 1, wherein the discontinuity in the at least one conductive ring defining the non-conducive portion comprises a non-conductive material.

4. The soft-field tomography system of claim 1 wherein the discontinuity in the at least one conductive ring defining the non-conductive portion comprises a gap.

5. The soft-field tomography system of claim 1, wherein the at least one conductive ring further comprises at least two discontinuities that define a major conductive arc and a minor conductive arc in the conductive rings, wherein the major and minor conductive arcs extend around the object.

6. The soft-field tomography system of claim 5, wherein the minor arc and the non-conductive portions encompass shout two degrees of the conductive rings.

7. The soft-field tomography system of claim 1, wherein the object is a pipe in a non-vertical orientation and having fluid flowing therethrough, the at least one conductive ring positioned within the pipe with the non-conductive portion positioned within the flowing fluid such that the non-conductive portion is in continuous contact with the fluid.

8. The soft-field tomography system of claim 1, wherein the one or more excitation drivers are configured to apply the excitation signals during an excitation sequence, wherein the excitation sequence is based on an application that is optimized using at least one of a signal-to-noise ratio, a resolution, a detection capability, an instrumentation complexity or an acquisition speed.

9. The soft-field tomography system of claim 1, wherein the property distribution is a distribution as determined in one or more of Electrical Impedance Spectroscopy (EIS), Electrical Impedance Tomography (EIT); Electrical Resistance Tomography (ERT) or Electrical Capacitance Tomography (ECT).

10. The soft-field tomography system of claim 1, wherein the property distribution comprises a distribution of one or more of electrical conductivity or electrical permittivity.

11. A soft-field tomography system comprising:
a plurality of transducers configured for positioning proximate a surface of an object and spaced apart around the object; at least a subset of the transducers asymmetrically distributed relative to at least another subset of the transducers, wherein the asymmetric transducers in the subsets of transducers;
one or more excitation drivers coupled to the plurality of transducers and configured to generate excitation signals for the plurality of transducers;
one or more response detectors coupled to the plurality of transducers and configured to measure a response of the object at the plurality of transducers to the excitation applied by the plurality of transducers based on the excitation signals; and
a soft-field reconstruction module configured to reconstruct a property distribution based on the excitation signals and the measured response.

12. The soft-field tomography system of claim 11, wherein the transducers form two measurement rings spaced apart along the object, where each of the rings extends around the object.

13. The soft-field tomography system of claim 11, wherein the plurality of transducers comprise at least one of elliptical shaped electrodes, diamond shaped electrodes or triangular shaped electrodes.

14. The soft-field tomography system of claim 13, wherein the electrodes are arranged in different orientations or directions.

15. The soft-field tomography system of claim 11, wherein the object is a pipe in a non-vertical orientation and having fluid flowing therethrough, at least some of the subset of transducers positioned within the flowing fluid to be in continuous contact with the fluid, the subset of transducers having a greater density of distribution than the other subset of transducers.

16. The soft-field tomography system of claim 11, wherein the one or more excitation drivers are configured to generate excitations having at least one of a different phase or amplitude and apply the varying phase or amplitude excitations to the subsets of transducers, wherein a variance of the phase or amplitude between excitations applied to the transducers in the subset of transducers is different than a variance of the phase or amplitude between excitations applied to the transducers in the other subset of transducers.

17. The soft-field tomography system of claim 11, wherein the one or more excitation drivers are configured to apply the excitation signals during an excitation sequence, wherein the excitation sequence is based on an application that is optimized using at least one of a transducer distribution, a signal-to-noise ratio, a resolution, a detection capability, an instrumentation complexity or an acquisition speed.

18. The soft-field tomography system of claim 11, wherein the property distribution is a distribution as determined in one or more of Electrical Impedance Spectroscopy (EIS), Electrical Impedance Tomography (EIT), Electrical Resistance Tomography (ERT) or Electrical Capacitance Tomography (ECT).

19. The soft field tomography system of claim 11, wherein the property distribution comprises a distribution of one or more of electrical conductivity or electrical permittivity.

20. A soft-field tomography system comprising:
a transducer configuration for positioning proximate a surface of an object and spaced along a circumference of the object, the transducer configuration including a conductive strip including a plurality of measurement regions defined by electrodes, at least one of the electrodes surrounded by a non-conductive ring portion, the conductive strip formed from an electrically conductive material and wherein the non-conductive ring portion is surrounded by the electrically conductive material of the conductive strip;
one or more excitation drivers coupled to the electrodes and configured to generate excitation signals for the electrodes;
one or more response detectors coupled to the electrodes and configured to measure a response of the object at the electrodes to the excitation applied by the electrodes based on the excitation signals; and
a soft-field reconstruction module configured to reconstruct a property distribution based on the excitation signals and the measured response.

21. The soft-field tomography system of claim 20, wherein the object is a pipe and the conductive strip defines a ring configured to extend around an inner circumference of the pipe and the electrodes are asymmetrically distributed along the conductive strip.

22. The soft-field tomography system of claim 20, wherein the object is a pipe M anon-vertical orientation and having fluid flowing therethrough, at least some of a subset of electrodes positioned within the flowing fluid to be in continuous contact with the fluid, the subset of transducers having a greater density of distribution than another subset of transducers.

* * * * *

UNITED STATES PATENT AND TRADEMARK OFFICE
CERTIFICATE OF CORRECTION

PATENT NO. : 8,963,562 B2
APPLICATION NO. : 13/222825
DATED : February 24, 2015
INVENTOR(S) : Basu et al.

It is certified that error appears in the above-identified patent and that said Letters Patent is hereby corrected as shown below:

In the specification,

In Column 1, Line 59, delete "Soft-field" and insert -- soft-field --, therefor.

In Column 4, Line 14, delete "(a)" and insert -- ($\sigma$) --, therefor.

In Column 13, Line 23, delete "(CPUs)," and insert -- (GPUs), --, therefor.

In the claims,

In Column 14, Line 60, in Claim 4, delete "claim 1" and insert -- claim 1, --, therefor.

In Column 15, Line 3, in Claim 6, delete "shout" and insert -- about --, therefor.

In Column 15, Line 29, in Claim 11, delete "object;" and insert -- object, --, therefor.

In Column 15, Lines 31-32, in Claim 11, delete "transducers in the subsets of transducers;" and insert -- transducers, wherein the asymmetric distribution includes at least one of a different size or a different shape of the plurality of transducers in the subsets of transducers; --, therefor.

In Column 16, Line 55, in Claim 22, delete "pipe M anon-vertical" and insert -- pipe in a non-vertical --, therefor.

Signed and Sealed this
Twentieth Day of October, 2015

Michelle K. Lee
*Director of the United States Patent and Trademark Office*